(12) United States Patent
Skinner et al.

(10) Patent No.: US 7,572,642 B2
(45) Date of Patent: Aug. 11, 2009

(54) ASSAY BASED ON PARTICLES, WHICH SPECIFICALLY BIND WITH TARGETS IN SPATIALLY DISTRIBUTED CHARACTERISTIC PATTERNS

(75) Inventors: Nigel G. Skinner, Winchester, MA (US); Paul Fenton, Marblehead, MA (US); George A. Adaniya, Wellesley, MA (US)

(73) Assignee: Ambrigen, LLC, Beverly, MA (US)

( * ) Notice: Subject to any disclaimer, the term of this patent is extended or adjusted under 35 U.S.C. 154(b) by 77 days.

(21) Appl. No.: 10/125,102

(22) Filed: Apr. 17, 2002

(65) Prior Publication Data
US 2002/0155490 A1 Oct. 24, 2002

Related U.S. Application Data

(60) Provisional application No. 60/284,706, filed on Apr. 18, 2001.

(51) Int. Cl.
*G01N 33/543* (2006.01)
(52) U.S. Cl. .................. 436/518; 436/524; 436/527; 436/528; 436/531; 436/532; 436/533; 436/534; 436/56; 436/164; 436/166
(58) Field of Classification Search .................. None
See application file for complete search history.

(56) References Cited

U.S. PATENT DOCUMENTS

| | | | |
|---|---|---|---|
| 4,383,031 A | 5/1983 | Boguslaski et al. |
| 5,580,749 A | 12/1996 | Hughes |
| 5,653,859 A | 8/1997 | Parton et al. |
| 5,656,207 A | 8/1997 | Woodhead et al. |
| 5,683,888 A | 11/1997 | Campbell |
| 5,736,320 A | 4/1998 | Schlederer et al. |
| 5,736,330 A | 4/1998 | Fulton |
| 5,741,462 A | 4/1998 | Nova et al. |

(Continued)

FOREIGN PATENT DOCUMENTS

EP 1 018 365 7/2000

(Continued)

OTHER PUBLICATIONS

"What is chemiluminescence?" http://www.lumigen.com/documents/chemexplained.shtml.*

(Continued)

*Primary Examiner*—Yelena G Gakh
(74) *Attorney, Agent, or Firm*—Pandiscio & Pandiscio

(57) ABSTRACT

The invention provides a particle comprising a surface, wherein a portion of the surface is capable of emitting electromagnetic radiation and another portion of the surface is capable of emitting a differential electromagnetic radiation (either different intensity, different frequency or no radiation), and wherein the arrangement of said portions of the surface defines a spatially distributed code for identifying the particle. The invention also provides method of manufacturing a particle having an identifying code comprising providing a particle with a functionalized surface which comprises functional binding moieties and selectively removing a plurality of the functional binding moieties from the surface to create a pattern of functionalized and differentially-functionalized zones on the surface. Various liquid-based assay methods employing the particle of the invention and a kit comprising the particle of the invention are also disclosed.

28 Claims, 4 Drawing Sheets

U.S. PATENT DOCUMENTS

| | | | |
|---|---|---|---|
| 5,751,629 | A | 5/1998 | Nova et al. |
| 5,770,455 | A | 6/1998 | Cargill et al. |
| 5,858,802 | A | 1/1999 | Chai-Gao et al. |
| 5,874,214 | A | 2/1999 | Nova et al. |
| 5,925,562 | A | 7/1999 | Nova et al. |
| 5,958,713 | A | 9/1999 | Thastrup et al. |
| 5,981,180 | A | 11/1999 | Chandler et al. |
| 6,008,057 | A | 12/1999 | Glass et al. |
| 6,023,540 | A | 2/2000 | Walt et al. |
| 6,034,775 | A | 3/2000 | McFarland et al. |
| 6,046,003 | A | 4/2000 | Mandecki |
| 6,057,107 | A | 5/2000 | Fulton |
| 6,057,456 | A | 5/2000 | Hartwig et al. |
| 6,087,186 | A | 7/2000 | Cargill et al. |
| 6,117,643 | A | 9/2000 | Simpson et al. |
| 6,147,159 | A | 11/2000 | Hu et al. |
| 6,232,066 | B1 | 5/2001 | Felder et al. |
| 6,242,246 | B1 * | 6/2001 | Gold et al. ............... 435/287.1 |
| 6,242,583 | B1 | 6/2001 | Schmidt et al. |
| 6,248,540 | B1 | 6/2001 | Weinberg et al. |
| 6,258,454 | B1 | 7/2001 | Lefkowitz et al. |
| 6,268,222 | B1 | 7/2001 | Chandler et al. |
| 6,274,323 | B1 | 8/2001 | Bruchez et al. |
| 6,291,669 | B1 | 9/2001 | Kwiatkowski et al. |
| 6,316,180 | B1 | 11/2001 | Martin |
| 6,340,588 | B1 | 1/2002 | Nova et al. |
| 6,350,588 | B1 | 2/2002 | Roth et al. |
| 6,352,828 | B1 | 3/2002 | Brenner |
| 6,355,490 | B1 | 3/2002 | Hochlowski et al. |
| 6,362,009 | B1 | 3/2002 | Munoz et al. |
| 6,366,354 | B1 | 4/2002 | Chandler |
| 2003/0129654 | A1 * | 7/2003 | Ravkin et al. ............ 435/7.1 |

FOREIGN PATENT DOCUMENTS

| | | |
|---|---|---|
| GB | 1 568 699 | 6/1980 |
| GB | 2 306 484 | 5/1997 |
| GB | 2 318 666 | 4/1998 |
| GB | 2 289 150 | 7/1998 |
| WO | WO 94/09372 | 4/1994 |
| WO | WO 96/24061 | 8/1996 |
| WO | WO 96/36436 | 11/1996 |
| WO | WO 97/15390 | 5/1997 |
| WO | WO 99/67641 | 12/1999 |
| WO | WO 00/39587 | 7/2000 |
| WO | WO 00/44491 | 8/2000 |
| WO | WO 00/47996 | 8/2000 |
| WO | WO 00/48000 | 8/2000 |
| WO | WO 00/63437 | 10/2000 |
| WO | WO 00/65472 | 11/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/02374 | 1/2001 |
| WO | WO 01/08081 | 2/2001 |
| WO | WO 01/18524 | 3/2001 |
| WO | WO 01/25510 | 4/2001 |
| WO | WO 01/26038 | 4/2001 |
| WO | WO 01/46675 | 6/2001 |
| WO | WO 01/57268 | 8/2001 |
| WO | WO 01/57269 | 8/2001 |
| WO | WO 01/59432 | 8/2001 |
| WO | WO 01/61043 | 8/2001 |
| WO | WO 01/78889 | 10/2001 |
| WO | WO 02/00336 | 1/2002 |
| WO | WO 02/12897 | 2/2002 |
| WO | WO 02/16649 | 2/2002 |
| WO | WO 02/21128 | 3/2002 |

OTHER PUBLICATIONS

Stojanovic et al. "Novel, light-emitting reaction of (E)-2-(phenylsulfonyl)-3-phenyloxaziridine with strong basis",J. Am. Chem. Soc., 1995, v. 117, pp. 9921-9922.*
Helmenstine "Light stick colors", http://chemistry.about.com/library/weekly/aa031703a.htm.*
Amarnath and Broom (1977). *Chem. Rev.* 77: 183-217.
Atherton and Sheppard In *Prospectives in Peptide Chemistry*, ed. Karger, 101-117 (1981).
Cargill and Lebl (1997). *Curr. Opin. Chem. Biol.* 1: 67-71.
Elder et al. In *DNA Microarrays: A Practical Approach*, ed. Schena, Oxford University Press 77-99 (1999).
Fridkin In *The Peptides*, vol. 2, Chapter 3, Academic Press, Inc. 333-363 (1979).
Furka et al. (2000). *J. Comb. Chem.* 2: 220-223.
Gruber et al. (2000). *Bioconjugate Chem* 11: 696-704.
Lebl et al. (1995). *Biopolymers(Peptide Science)* 37: 177-198.
Merrifield (1963). *J Am Chem Soc* 85: 2149-2154.
Randolph et al. (1997). *Nuc Acids Res* 25: 2923-2929.
Stikeman (2002). *Technology Review* January/February: 22.
Borman (1998) *Chemical & Engineering News* Combination Chemistry.
Nicolaou et al. (1995). *Angew. Chem.* 107: 2476-2479, No English Abstract.
International Search Report for PCT/US02/12271, mailed Sep. 19, 2002.

* cited by examiner

FIGURE 1A Micro-extrude polymer filament

FIGURE 1B Plasma treat polymer to activate surface

FIGURE 1C Etch code into filament with UV-excimer laser

FIGURE 1D Singulate filament to obtain particles

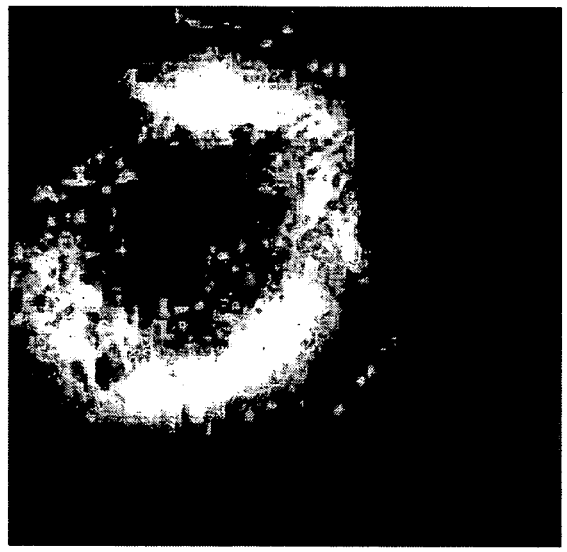
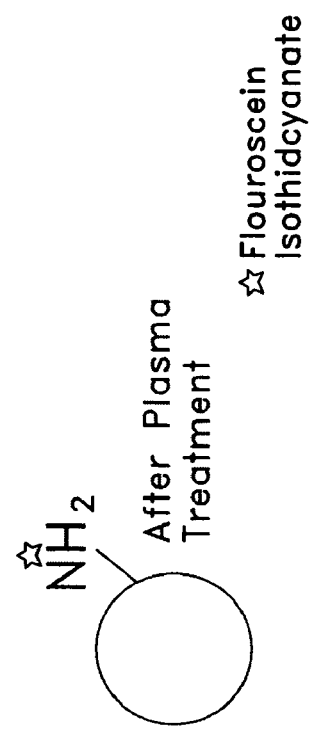
FIGURE 4B
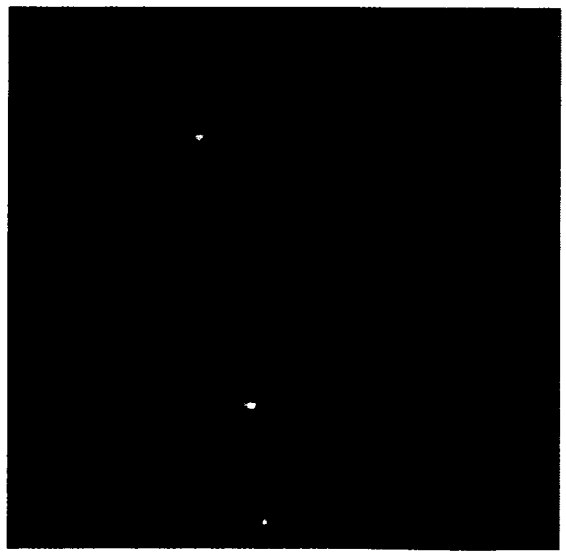
FIGURE 4A

ASSAY BASED ON PARTICLES, WHICH SPECIFICALLY BIND WITH TARGETS IN SPATIALLY DISTRIBUTED CHARACTERISTIC PATTERNS

RELATED APPLICATION

This application claims priority to U.S. Provisional Application No. 60/284,706, filed Apr. 18, 2001. The contents of that application in its entirety are hereby incorporated by reference into this specification.

BACKGROUND OF THE INVENTION

1. Field of the Invention

The present invention relates generally to devices and methods for screening, selecting, and validating small molecule and biologic drug candidates in solution and, more particularly, to spatially distributed identification tags that facilitate the direct quantitative, semi-quantitative, or qualitative assay of proteins, genes and their biologic products (carbohydrates, lipids or other cellular components).

2. Related Art

All patents and publications cited throughout the specification are hereby incorporated by reference into this specification in their entirety in order to more fully describe the state of the art to which this invention pertains.

The mapping of the human genome, currently believed to comprise of some thirty thousand genes, has led to an exponential growth in data available to pharmaceutical companies. The linkage between specific genes and disease processes, namely functional genomics, will, it is believed, provide a means of better screening small molecule libraries against druggable genes (genes that are believed to be functionally related to a specific disease). Small molecules will be selected on the basis of their ability to influence the expression profile of the messenger RNA (mRNA) of such genes. There are, however, limitations to such selection strategies. Firstly, the strategy assumes that all gene products are known and can be assayed; secondly, the strategy assumes a one to one relationship between gene and protein. The occurrence of gene-splice variants in all but infectious diseases and prokaryotic species belies the former assumption, whilst post-translational modification (e.g., glycosylation, phosphorylation, acetylation) of proteins as well as environmental parameters obviate the latter assumption. As a consequence of these limitations, proteomics, whose aim is the mapping of proteins, protein-protein interactions, and their metabolic, catabolic, and anabolic pathways, has grown in significance as a means of facilitating the selection of small molecules, and biologics (e.g., protein therapeutics, monoclonal antibodies, vaccines, therapeutic serum or gene transfer products), against a growing number of established, and yet to be established, protein targets. The emerging field of proteomics is estimated to yield in excess of 10,000 proteins during this decade. Identification and validation of these potential targets will require substantial equipment, supplies for testing in-vitro with cell based assays, in-vivo with animal models and eventually with human clinical trials in order to ensure drug discovery and subsequent development.

Such testing requires small molecules or biologics to be screened against samples of tissue and physiological fluids, comprising the protein, genes, or other biological (carbohydrate, lipid) targets of interest. Such samples can be costly and difficult to access, often requiring a priori confirmation that the testing to be conducted is therapeutically relevant and justified. A blood sample likely contains greater than 10,000 protein targets, yet existing instrumentation and assay methodology limits the number that can be realistically used as targets to a far smaller figure. A pharmaceutical company will typically screen all of its small molecule against less than one percent of this figure, necessarily eliminating many potential drug targets, and possible drug candidates.

This strategy requires sophisticated instrumentation that can purify drug leads, screen the vast number of leads with their protein targets, and analyze and interpret the results. The primary methods used typically involve each or a combination of the following: liquid chromatography (LC) an expensive but well established method primarily for the distillation of drug leads, 2d (Isoelectric Focusing) and 1d-gel electrophoresis (SDS-PAGE), yeast 2-hybrid systems, mass spectrometry (MS), and various types of immunoassay. All of these methods involve well established but costly instrumentation, requiring specialist expertise for their operation and interpretation of data. These methods do not provide, either individually or collectively, a method of rapidly screening a massive number of small molecules or biologics against an equally massive number of protein targets. This is, in part, due to the fact that not all protein targets are known. 2d-gel electrophoresis is the primary method for the mapping out of proteins (estimated at between 60,000 to 150,000 per mammal) but has resolution limits imposed by the distance between spots and the protein loading per spot, thus significantly limiting the technique to high abundance proteins. This is a severe limitation given that many low abundance proteins are believed to play key roles in cellular signaling and disease pathways, and that protein activity provides more therapeutically valuable information than protein abundance. Moreover proteins often do not act alone. An increasing effort is being spent on examining how proteins interact, not only with other proteins but also with nucleic acid, small molecules and ligands. A current popular method is to use antibodies as capture molecules to trap interacting proteins. The immunoprecipitate is then run out on a 1-D gel, digested and analyzed by tandem MS to determine the identity of the interacting partners. Yeast 2-hybrid systems are powerful tools for the identification of protein-protein and protein-DNA interactions, although they are hampered by high rates of false positives, a poor ability to identify weak interactions, a relatively low throughput and are not suited generally to the study of protein-ligand interactions. MS requires "clean" samples and is not good at analyzing protein complexes. Inmunoassays provide a means of determining the kinetics and cross-reactivities associated with the binding of drug targets to drug compounds. They are usually conducted in microtiter plates of either 96-well or 384-well format. However, the serial nature of this process combined with the requirement for washing, incubation, and heavy reagent consumption, mean that this is a costly and time-consuming process.

There is a strong drive for technologies that facilitate (i) the cost effective identification of proteins and their interactions with other proteins, as well as the role they play in metabolic, catabolic, and anabolic pathways; (ii) the cost effective profiling of proteins in terms of abundance and/or activity; (iii) the cost effective screening of massive numbers of small molecules and biologics against selected proteins.

Such technologies typically require a combination of speed, low reagent and sample consumption, multiplexing (i.e., analysis of multiple targets in parallel), low cost (particularly relating to any disposable elements), high assay repeatability, robust biochemical surfaces, and high sensitivity & selectivity. These requirements resulted in the development of protein microarrays which provide a means of mass producing surfaces, of typically a few centimeters square, comprising of a massive number of multiple target probes, usually proteins that are specific to, and bind to, known target proteins such as monoclonal antibodies (MABs). Much of this technology has evolved from gene microarrays. However, in contrast to gene arrays, where probes are typically synthetic oligonucleotides, protein microarrays suffer a number of important disadvantages: denaturation of complex protein structure due to either the protein attachment process and/or storage conditions; sensitivity and selectivity, due to the affinity and cross-reactivity of the binder protein used; and cost, due to the nature of the mass manufacturing technology used, often based on either silicon or a special glass. Furthermore, relative to the in situ synthesis of oligonucleotides, specific to target DNA/RNA, and used for the sequencing of DNA, identification of mutations (such as single nucleotide polymorphisms, SNPs), proteins cannot be built up in such a way. In situ synthesis of amino acids has been attempted but without any commercial success to date and needs to be added to a surface in a preformed fashion, i.e. as complete antibodies, mimics, or other form of binder protein. This necessarily limits the speed at which the process can be achieved, increases the costs, and requires access to such binder proteins.

In all cases, conventional approaches rely on a priori knowledge of target proteins and pathways in order to develop binder proteins, that form the basis of the biochemical probe arrays used to query those targets, and gain information on, for example, drug (small molecule, biologic) efficacy and toxicity.

The in situ synthesis of oligonucleotide arrays onto silicon substrates via the use of photo-labile groups and a series of masking and demasking steps, allowed Affymetrix to develop and produce its GeneChip™. This technology has provided a method of mass-producing such arrays on silicon using technology largely inherited from the semiconductor industry. These chips are, however, expensive, require lead times of up to one month, and provide oligomers of a limited number of bases. They also require a priori knowledge of the target genes. The length of the oligomers is limited by the photoactivation process used. It means that yield would be very poor for oligomers of greater than 25 bases in length. This significantly limits the sensitivity of this method for application such as gene-expression profiling, where only abundant genes are detected and not low copy numbers of genes, or in some cases their splice variants. This shortcoming can be circumvented by PCR amplification of the expressed RNA, however, artifacts are known to be created by such processes along with the fact that the biases introduced by PCR must be accounted for in the interpretation of results and gene expression profiling methodology used. The limited flexibility and high access costs associated with Affymetrix's technology have resulted in a number of companies, and users, producing glass-slide based arrays. This has been due in part to the increasing availability of so-called arrayers and spotters that, by various dispensing methods (e.g., ink-jets and pins) can deposit oligonucleotide or protein probe-containing reagents onto various substrates, and using a variety of surface chemistries and functional groups (e.g., amines and aldehydes, and the like) attach these probes to the surface. One method developed by Rosetta provides an efficient method of ink-jet printing nucleotide bases onto a substrate, which are subsequently in situ synthesized using conventional phosphoramidite chemistry, which does not suffer the aforementioned shortcomings of the Affymetrix approach.

Despite significant growth in the use of these microarray-based systems, limits in the applicability of these systems have led to dissatisfaction among users and many pharmaceutical companies have expressed interest in alternative methods of achieving high throughput screening.

Bead-based assays have therefore been developed which overcome the limitations of the microarray technology. The superior mixing in a bead-based array results in negligible mass transfer of target to bead, as opposed to microarrays where target diffusion is always mass-transfer limited. This results in faster time-to-result, reduced need for washing, and improved signal to noise ratios. Bead-based arrays also allow for greater spatial independence relative to microarrays, where probes occupy a fixed position on a substrate and cannot be individually manipulated. Such advantages are not only of interest to the tracking and manipulation of compounds in combinatorial libraries, but also to assays for application in diagnostics, prognostics, and drug discovery.

Luminex has developed a particle-based assay format employing micron-scale microspheres, whose coding is achieved through the mixing of two different fluorochromes (incorporated into polystyrene particles) in different molecular weight ratios. See, e.g., U.S. Pat. Nos. 6,268,222 and 5,736,330. Luminex has achieved 64 different codes by this method. A higher number of codes would require the use of 3 or more different fluorochromes. Spectral discrimination of codes becomes more challenging as do the costs associated with manufacturing the particles. Some coding schemes employ fluorescent spectra as a means of distinguishing particles. This can present a problem in media where background fluorescence occurs in the same frequency range as the coding. Such a situation would include the assay of various proteins in whole blood. Alternative approaches, currently under development, include that of Quantum Dot whose coded particles are distinguished by very narrow symmetric emission spectra, obtained by the nanometric tuning of semiconductor nanocrystals. See, e.g., U.S. Pat. No. 6,274,323. Also, SurroMed, discloses particles that are electroplated into the pores of an alumina membrane to which a silver electrode has been evaporated. See, e.g., WO 01/02374 and WO 00/65472. In the case of SurroMed, metals exhibiting different reflectivities are electro-deposited into these pores. The codes are provided by differential reflectivity. However, these technologies have limitations in practice, including the fact that attachment of proteins on semiconductor nanocrystals is non-trivial and tends to denaturation, and the utilization of metal substrates (such as by SurroMed) facilitates non-specific adsorption of non-target proteins, as well as limitations in their applicability such as the fact that presenting a reflectance-based code on a particle would be difficult to read in turbid media such as whole blood.

Finally, particle-based assay formats are typically run through flow cytometer instruments. Most of the above described particle based formats, however, require customized cytometers due to the need to detect optical emissions at different wavelengths to those that result solely from the binding of, for example, an antibody to an antigen (e.g. an antibiotic), and the subsequent attachment of a reporter antibody, to which is attached a fluorophore. Conventional sandwich immunoassay involves the washing of beads to which antigen and reporters have bound followed by excitation of the bead by a suitable wavelength source such that binding events could be detected, and in the case of a dose-response assay, quantitation of analyte measured at a specific point in time following exposure of antibody to antigen, through the relationship between emission intensity and analyte (target) concentration.

SUMMARY OF THE INVENTION

This invention provides a particle comprising a surface, wherein a portion of the surface is capable of emitting a first electromagnetic radiation and another portion of the surface is capable of emitting a differential electromagnetic radiation, and wherein the arrangement of said portions of the surface defines a spatially distributed code for identifying the particle. In the practice of the invention, the differential electromagnetic radiation may comprise electromagnetic radiation of a different intensity or a different frequency than the first electromagnetic radiation or can be no electromagnetic radiation at all.

This invention further provides a method of manufacturing a particle having an identifying code comprising providing a particle having a functionalized surface which comprises functional binding moieties and selectively removing a plurality of the functional binding moieties from the surface to create a pattern of functionalized and differentially-functionalized zones on the surface.

This invention also provides a method of manufacturing a particle having an identifying code comprising providing a particle having a differentially-functionalized surface and selectively adding a plurality of functional binding moieties to the surface to create a pattern of functionalized and differentially-functionalized zones on the surface.

The invention further provides a particle comprising a surface wherein the surface comprises at least one modified portion comprising a plurality of functional binding moieties and at least one unmodified portion which is substantially free of functional binding moieties, wherein the modified portion(s) further comprise an electromagnetic radiation emitting species, and wherein the arrangement of modified and unmodified portions on the surface forms a pattern amenable to detection.

The invention also provides an article of manufacture having a substantially cylindrical shape with a diameter between about 5 μm and 200 μm, and a length between about 10 μm and 2000 μm, wherein the surface of the particle comprises at least one substantially circumferential functionalized zone, at least one substantially circumferential differentially-functionalized zone between the end of the particle and the functionalized portion or between functionalized portions, and a combination of the width(s) of the functionalized portion(s) and the width(s) of the differentially-functionalized zone(s) establishes a code for identifying the particle.

The invention further provides a labeled oligonucleotide library comprising a plurality of oligonucleotide compounds attached to a plurality of particles of the invention. In certain embodiments, each particle of the labeled oligonucleotide library contains a single species of oligonucleotide compound. The oligonucleotide compounds can be naturally-occurring, synthetic or semi-synthetic oligonucleotides.

The invention also provides a method of determining the sequence of an unknown oligonucleotide species in a solution comprising providing a labeled oligonucleotide library of the invention, wherein the oligonucleotide sequence of each oligonucleotide attached to each particle in the library and the characteristic electromagnetic emission intensity profile of each particle in the library is stored and correlated in a database, mixing the solution with the labeled oligonucleotide library under conditions sufficient to permit the unknown oligonucleotide speices to hybridize with corresponding particles of the labeled oligonucleotide library, exciting the particles to produce the characteristic electromagnetic emission intensity profile corresponding to the particle(s) in the library, detecting the characteristic electromagnetic emission intensity profile and correlating it to the characteristic emission intensity profile in the database, thereby determining the sequence of the unknown oligonucleotide species.

The invention further provides a method for determining the amount of a target compound in a test sample comprising the steps of incubating a mixture of a test sample suspected of containing the target compound with at least one particle according to the invention wherein the particle(s) comprise a plurality of an antibody which is specific for the target compound, under conditions appropriate to form target/antibody complexes, wherein the electromagnetic radiation emission occurs upon formation of the target/antibody complex, and measuring the amount of electromagnetic radiation present in said mixture thereby determining the amount of target compound in said test sample.

The invention also provides an assay for the detection of binding between a probe and a target comprising contacting the probe with a solution suspected of containing the target, wherein the probe is attached to a particle which emits electromagnetic radiation upon binding between probe and target and emits electromagnetic radiation as a means of identifying the particle in solution.

Finally, the invention provides a kit for the detection of binding between a probe and a target comprising at least one particle of the invention and a flow cytometric device.

BRIEF DESCRIPTION OF THE FIGURES

FIGS. 4(A) and (B) illustrate the surface functionalization of the particle material according to the invention. FIG. 3(A) shows a polypropylene material surface prior to plasma treatment and FIG. 3(B) shows the polypropylene material surface following plasma treatment.

DETAILED DESCRIPTION OF THE INVENTION

The present invention is directed to particle tags useful for identifying molecules in liquid-based assay systems. Each particle has a surface comprising a plurality of functional binding moieties in selected areas, such that the surface comprises zones of functionalized material interspersed with zones of differentially-functionalized material. The functionalized zones further comprise a moiety that emits electromagnetic radiation, typically upon reaction or excitation from another source of energy. The functionalized and differentially-functionalized zones are spaced in such a way on the particle surface so as to create a pattern providing a spatially distributed code for identifying the particle. The code is "read" by detecting the pattern of electromagnetic radiation emitted in the functionalized zones. The code can be stored in a database for comparison with data from tracked particles in an assay to determine the identity of a molecule attached to the functional binding moiety on a particle. The electromagnetic radiation emitting moiety may be attached directly to the particle in the functionalized zones or may be attached to the molecule attached to the functional binding moieties in the functionalized zones.

Figure 1:
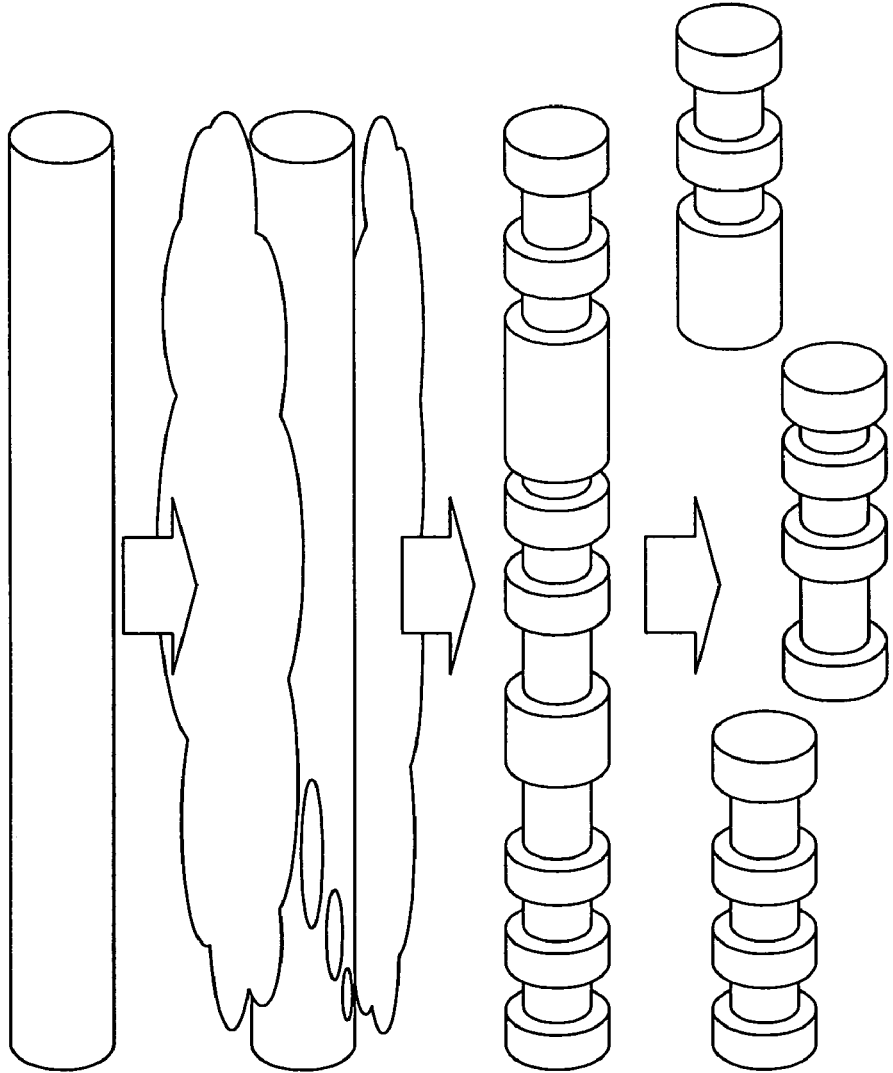
FIGS. 1(A) to 1(D) illustrates an example of the process of extrusion, functionalization and coding of the surface of a filament, and its subsequent singulation into individual particles.

In a preferred embodiment, the particle is formed in the shape of cylinder of polymeric material and the coding of the particle is in the form of a series of bands of functionalized binding moieties alternating with bands containing non-functionalized binding moieties. In a preferred manufacturing method, the polymeric material is extruded as a filament (FIG. 1A), functionalized by a plasma treatment (FIG. 1B), selectively ablated to create the non-functionalized bands (FIG. 1C), and singulated or cut into pieces, (FIG. 1D) to create the cylindrical particles with a spatially distribute code for identifying each particle.

As explained in detail herein, a catalog or library of particles can be used to track and/or identify target compounds in solution by identifying the particle to which a probe and electromagnetic radiation emitting species is attached when a binding event between the probe and the target causes the electromagnetic radiation emission. The particles of the invention can be used to identify unknown samples comprising, for example, a fluorophor-labeled protein or nucleic acid. In the case of an assay for detecting a protein target suspected of being in solution, the probe may comprise a known receptor for the protein and a fluorophor-labeled secondary antibody could also be added to the sample for the purposes of a sandwich assay. In the case of an unknown nucleotide sequence, a fully degenerate set of fluorophor labeled complementary nucleotide probes may be used to detect a binding event that would trigger emission of the flurorophor. After being mixed with the unknown protein or nucleic acid in the sample, the particles are flowed past a suitable light source (e.g. a laser). If any of the protein or nucleic sample binds with a corresponding antibody/mimic or oligonucleotide sequence probe attached to one of the coded particles, the fluorophore will give off energy at each of the functionalized zones of the particle, which can then be detected by, for example, a suitable optical reader system (e.g. PMT, CCD). Because each peak of energy from each functionalized zone will be separated by a particular distance from a differentially-functionalized zone, the detector produces a resultant waveform for each particle. Each particle will have a spatially distributed pattern of functionalized and differentially-functionalized zones, the pattern being determined by, for example, the width and spacing of such zones. A computer can be employed to compare the distances between the peaks of the waveform detected in the sample, to the waveform of cataloged particles to identify the particular cataloged particle which has bound to the sample. Once the particle is identified in the database, the identity of the unknown protein or nucleic acid within the sample is determined.

I. Particle Tags.

This invention provides a particle comprising a surface, wherein a portion of the surface is capable of emitting a first electromagnetic radiation and another portion of the surface is capable of emitting a differential electromagnetic radiation, and wherein the arrangement of said portions of the surface defines a spatially distributed code for identifying the particle. As used herein, the term "differential electromagnetic radiation" can mean, for example, electromagnetic radiation of a different intensity or different frequency than the first electromagnetic radiation or can be absence or near absence of electromagnetic radiation. In a preferred embodiment, the differential electromagnetic radiation is the absence or near absence of electromagnetic radiation. The particles of the invention are typically formed from a mass of material. The material preferably has a specific gravity such that the particles formed there from are iso-buoyant in the carrier fluid used in, for example, a flow cytometer (comparable to the density of water; i.e., 1.0 g/cm$^3$). Such a density avoids particles created from the material from sedimenting out or floating. This density also allows the particles to maintain lateral flow in a flow cytometer's liquid-handling system or any similar system used to track and identify the particles. Moreover, the material should include such characteristics that result in particles that are non-aggregating. Specifically, the resulting particles should not aggregate or form clusters since clustered particles would create difficulty in distinguishing one particle from another. Further, the particles should be resistant to attractive forces such as electrostatic charge and ideally have a surface which is highly inert in its natural state, unless activated. In addition, the particle material preferably has a low intrinsic electromagnetic radiation emission, so as to reduce interference with the electromagnetic radiation of the coding and maximize the signal to noise ratio.

Preferred examples of the types of materials having the above-identified properties that can be formed into particles according to the present invention include materials chosen from the group consisting of polymers, composites, inorganics, natural products, and combinations thereof. The polymer material useful in the present invention can comprise electrically non-conducting or conducting polymers. Examples of acceptable polymeric materials include but are not limited to polystyrene, halogenated polystyrene, polyaniline, polyacetylene, polypyrrole, polyacrylic acid, polyacrylonitrile, polyamide, polyacrylamide, polyacrolein, polybutadiene, polycaprolactone, polycarbonate, polyester, polyethylene, polypropylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, as well as cross-linked polystyrene such as with divinylbenzene, grafted copolymers such as polyethyleneglycol/polystyrene, dimethylacrylamide, which can also be cross-linked such as with N,N'-bis-acryloyl ethylene diamine, and any combinations thereof. Examples of "natural products", as used herein, include such material as carbohydrate, including carboxymethyl cellulose, hydroxyethyl cellulose, agar, gel, proteinaceous polymer, polypeptide, lipid, metal, resin, latex, rubber, silicone, e.g., polydimethyldiphenyl siloxane, glass, ceramic, charcoal, kaolinite, bentonite, silk, wax, rubber, resins, and the like. Examples of "composites" are those such as glass fiber composites, carbon fiber composites, and combinations thereof. Examples of "inorganic" materials, as used herein, include inorganic polymers, metal oxides (e.g., silica, alumina), mixed metal oxides, metal halides (e.g., magnesium chloride), minerals, quartz, zeolites, TEFLON, and the like. General reviews of useful materials for forming particles that include a covalently-linked reactive functionality can be found in Atherton et al., Prospectives in Peptide Chemistry, Karger, 101-117 (1981); Amamath et al., Chem. Rev., 77:183-217 (1977); and Fridkin, The Peptides, Vol. 2, Chapter 3, Academic Press, Inc., (1979), pp. 333-363.

Most preferred of these materials are polymeric materials. To create the particles from polymer material, the material is preferably first extruded, and then cold drawn, to produce a fine filament having a generally cylindrical cross-section with a predetermined diameter. Diameters of polymeric particles formed this way range generally between 1 μm and 1000 μm, and preferably between 10 μm and 50 μm, and most preferably approximately 20 μm.

Alternative methods of manufacture such as LIGA, hot (or UV) embossing, casting or injection moulding could also be employed to manufacture the particles of the invention. LIGA (Lithographie, Galvanoformung und Abformung, i.e. lithography, electroplating and moulding) is a three stage process which can be used for the manufacture of high aspect ratio, 3-D microstructures in a wide variety of materials, including polymers. Irradiating a resist (polymer) is the first step in the process. This can be achieved using laser light, electron or ion beams or X-rays from a synchrotron radiation source, the latter being essential for deep structures. Preferably, these methods use a shadow printing process. In the deep X-ray lithographic process a 2-D absorber pattern from a mask is transferred into the depth of a thick resist by the chemical changes induced by a highly collimated beam of X-rays. Development of the irradiated areas of the resist results in a 3-D replication of the pattern and a metallic master mould can then be produced by electroplating into the 'free' areas. In this variant of the method of making the particles of the invention, separate layers of polymer are deposited onto a flat substrate "master" such that cylinders are built up comprising "plasma functionalizable" and "non plasma-functionalizable" regions. The plasma non-functionalizable regions comprise a normally inert surface, such that on exposure to a plasma treatment process, only the plasma-functionalizable regions are functionalized. This could be achieved through the use of a photoresist with an optically modifiable surface or one whose starting surface is 100% occupied with a different functional group, thus is not conducive to further functionalization. These groups are effectively saturated (if necessary) by a process that does not effect the functionalizable/functionalized surface. In this instance both polymeric materials would exhibit a low auto-fluorescence.

Hot or UV embossing involves the transfer of structures, typically from an electroformed Nickel shim, into appropriate polymer materials (such as polycarbonate, PMMA, polystyrene). A further variant on the fabrication of the particles of the invention would modify polymeric shapes (e.g., cylindrical or rectangular) on a flat substrate by either heat or UV so as to remove or render inactive pre-defined areas of those surfaces (defined by the Nickel shim), following a plasma treatment activation stage.

Injection moulding, LIGA, or UV/hot embossing, or casting, could be used to mass produce many cylinders, or other appropriate polymer shapes, in parallel, that could then be plasma treated and selelctively functionalized with a UV-excimer laser.

The particle of the invention typically has a shape formed by designed extrusion die or can be free form. Preferred shapes include, but are not limited to, cylindrical, spherical, conical, elliptical, bar-like, slab-like, ribbon-like, ovoid, spiral, amoeba-like, or tube-like. The shapes are preferably solid but can be to a certain extent hollow provided they retain the general characteristics noted above. Preferred of these shapes are those having width and length dimensions that allow for the particle to have a surface that can be manipulated as described herein to provide the spatially distributed code. In one embodiment, the particle of the invention has an aspect ratio, of width to length, of from about 1:2 to about 1:10. In a preferred embodiment the particle has an aspect ratio of width to length of from about 1:3 to about 1:5. In an alternative embodiment, the particle is generally a sphere, i.e., having an aspect ratio of approximately 1:1. The aspect ratio chosen will substantially determine the proper horizontal orientation of the particle in its lateral flow through a detection instrument, for example the fluidic channel of a cytometer's detection head. The surface of the particle can be flat, curved, rough, smooth, or any combination thereof.

II. Electromagnetic Radiation.

Each of the particles formed according to the invention contains a spatially distributed code created by the arrangement on the surface of the particle of portions or areas or zones that emit a first electromagnetic radiation among portions or areas or zones that emit a differential electromagnetic radiation, i.e., electromagnetic radiation of, for example, a different frequency, a different intensity, or substantially no radiation. As explained in more detail below, the different zones are created on the surface of the particle by modification or functionalization of the surface to allow for selective attachment of sample molecules bearing electromagnetic radiation-emitting moieties or for attaching the electromagnetic radiation-emitting moieties directly to the surface. In a preferred embodiment, the electromagnetic radiation emitted by such moieties has a wavelength from infrared to ultraviolet so as to allow for detection by relatively inexpensive and widely available electromagnetic sensing means. Within this range, the preferred wavelengths are between 400 nm and 1 μm.

The electromagnetic radiation emitted by the moieties attached to the particles can be derived from optical or non-optical excitation of the moiety or combinations thereof. Examples of non-optical excitation include, but are not limited to, electrical, chemical, biological, electrochemical and combinations thereof. Preferred moieties that emit electromagnetic radiation include fluorescent tags, such as fluoroscein isothiocyanate (FITC), Texas Red; Cyanin 5 and Cyanin 5.5; and other fluorophores; electrochemiluminescent tags such as ruthenium tris bipyridyl salts, chemiluminescent tags such as CN, HF, HCF, and HCHO, and biochemiluminescent tags such as luciferase, luminol. Examples of bioluminescent proteins include fusion proteins containing GFP (see, e.g., U.S. Pat. No. 5,958,713) or luciferase, aequorin and obelin (see, e.g., U.S. Pat. No. 5,683,888). See also, U.S. Pat. No. 5,656,207, and references cited therein, discussing the use of chemiluminescent molecules, including acridinium and related compounds (e.g. phenanthridinium compounds), phthalhydrazides and related compounds (e.g. naphthalhydrazides), oxalate esters and related compounds and also stabilized dioxetanes and dioxetanones. Additional examples of these are well known in the art such as the disclosures of, and references contained in, U.S. Pat. No. 6,117,643 (bioluminescent species), U.S. Pat. No. 6,008,057 (fluorescent species); U.S. Pat. No. 4,383,031 (chemiluminescent and enzyme-catalzyed fluorescent species); and U.S. Pat. No. 6,316,180 (electrochemiluminescent species). Additional means of detection include colorimetric endpoint detection. In a preferred embodiment, to enhance signal-to-noise ratio of the electromagnetic radiation, CY3 fluorescence may be used. It has been observed that beyond a certain packing density, CY3 (absorbs at 550 nm and exhibits emission maxima at 570 nm) emission is amplified significantly (unlike CY5 which has been observed to have the opposite, quenching effect). (J. B. Randolph et al., Nucleic Acids Research, 25 (1997) 2923-2929; H. J. Gruber et al., Bioconjugate Chemistry, 11 (2000) 696-704). The creation of an optically readable code in a surface could also be achieved by inducing/modulating a variable strain in the material (in particular certain conducting polymers) where polymer sections subjected to a certain strain provide different responses to a given optical excitation.

III. Surface Functionalization/Modification.

Functionalization or modification of the surface of the particle as used herein refers to providing a means for covalently attaching sample molecules to the surface of the particles. Surface functionalization or modifications may include providing functional binding moieties on the surface of the material including, but not limited to, chemical moieties such as carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, silyl, siloxyl, disiloxyl, mesyl, tosyl, and glyoxal moieties. Additionally, the functional binding moiety can comprise providing a "cationic moiety" on the surface, which comprises any positively charged species capable of electrostatically binding to negatively charged sample molecules, such as polynucleotides. Examples of cationic moieties include, but are not limited to, polycations such as polylysine (e.g., poly-L-lysine), polyarginine, polyornithine, spermine, basic proteins such as histones, avidin, protamines, and modified albumins (e.g., N-acylurea albumin). The functional binding moiety may further include such reagents as antibodies, biotin, avidin, Ni-NTA to bind epitopes, botinylated molecules, hexahistidine tagged molecules, serum or collagen.

In the practice of the invention, the material from which the particles are made can be either modified to contain the functional binding moieties or may contain such functional binding moieties as inherent properties of the material. Methods of modifying the particle materials described above to contain such functional binding moieties are known to those of ordinary skill in the art, with references dating back to Merrifield's description of solid-phase synthesis (R. B. Merrifield, J. Am. Chem. Soc. 85 (1963) 2149). Such functional binding moieties can be cleavable but are preferably non-cleavable. Technologies developed for attaching compounds to solid substrates in combinatorial chemistry techniques and solid phase peptide synthesis and linkers used to attach oligonucleotides to support materials used in chip-based systems are equally applicable here. Examples of such technologies are discussed in U.S. Pat. Nos. 6,362,009; 6,355,490; 6,352,828; 6,258,454; 6,147,159; 6,248,540; 6,034,775; 6,291,669; 6,242,583; 6,232,066, and 6,057,456 and in the references disclosed therein.

In a preferred embodiment, surface functionalization or modification is conducted via an atmospheric plasma treatment using either a hydrazine or ammonia plasma, to attach amine functional binding moieties. The process is preferably conducted on polymeric material. This process can be optimized using modified gas flows and pressure in order to ensure homogeneous coverage of the filament surface with $NH_2$. In this method, gas molecules are accelerated and diffuse towards the target surface under the influence of electric and/or magnetic fields. Molecular bombardment knocks fragments of low molecular weight materials such as water, adsorbed gases and polymer fragments off the surface of the material to expose a fresh, clean surface. At the same time, a certain percentage of the reactive components of the plasma gas mixture have sufficient energy to bond to the freshly exposed surface resulting in the changing of the chemistry of the surface and imparting the desired functionality (e.g., primary amines attached via covalent bonds). This process typically produces an aminated surface layer less than 1 µm thick and tolerates solvents such as acetonitrile and strong acids. Indeed, all the conditions imposed by phosphoramidite oligonucleotide synthesis can be tolerated by the coating. Hydrazine and ammonia plasmas are good candidates for surface functionalization since it may be used with a wide range of polymers including polyesters, polycarbonates, and polyamides.

It is desirable that the functional binding moieties are added in a way to form a homogeneous, dense, coverage on the surface of the material in order to maximize binding of sample molecules to the resultant particle and, thereby, maximize an electromagnetic signal emanating from an attached electromagnetic emitting species. The layer should ideally not be too dense so as to cause steric hindrance problems. For example, when the sample molecule is nucleic acid and the particles are used to detect and identify binding in a sequencing reaction, steric hindrance may obstruct target nucleic acid during the binding process resulting in delayed or non-binding in a sample that otherwise could have bound.

IV. Sample Attachment.

Functionalization or modification provides a means of readily attaching a wide range of molecules to the surface of such materials which in turn provides for a wide applicability of the particles made from the materials. Such molecules are referred to herein as "probes" and include all substances with an affinity to target molecules or compounds whose presence, activity and/or amount in solution is desired to be determined and which have an affinity for a given probe. The "target" molecules can be man-made or naturally-occurring substances. Examples include, but are not limited to, small molecules, dyes, carbohydrates, lipids, cell products, receptors, ligands, agonists or antagonists which bind to specific receptors; polyclonal antibodies, monoclonal antibodies and antisera reactive with specific antigenic determinants such as on viruses, cells or other materials; drugs; nucleic acids or polynucleotides, including mRNA, tRNA, rRNA, oligonucleotides, DNA, viral RNA or DNA, ESTs, cDNA, PCR-amplified products derived from RNA or DNA, and mutations, variants or modifications thereof; proteins such as enzymes, substrates for enzymes; peptides; cofactors; sugars; polysaccharides; cells; cellular membranes; organelles; viruses; liposomes; microparticles; micelles; chemokines; lymphokines, and other substances which can be complexed, covalently bonded, or crosslinked with these substances described. As used herein, the terms nucleic acid, polynucleotide, polynucleic acid and oligonucleotide are interchangeable and include those species having normal ribose-phosphate backbones or backbones altered to enhance their properties as to attachment of labels, stability and half-life of such molecules.

The term "probe" as used herein refers to any substance, such as a molecule, that can be specifically recognized by a particular target. The types of potential probe/target or target/probe binding partners include receptor/ligand; ligand/antiligand; nucleic acid polynucleotide) interactions, including DNA/DNA, DNA/RNA, PNA (peptide nucleic acid)/nucleic acid; enzymes, other catalysts, or other substances, with substrates, small molecules or effector molecules; and the like. Examples of such probes include, but are not limited to, organic and inorganic materials or polymers, including metals, chelating agents or other compounds which interact specifically with metals, plastics, agonists and antagonists for cell membrane receptors, toxins and venoms, viral epitopes, hormones, hormone receptors, lipids, phospholipids, proteins, peptides, enzymes, enzyme substrates, cofactors, drugs, lectins, sugars, nucleic acids (such as defined above), oligosaccharides, polyclonal and monoclonal antibodies, single chain antibodies, or fragments thereof. Probe polymers can be linear or cyclic. Any of the substances described above as "probes" can also serve as a "targets," and vice-versa.

In a preferred embodiment, oligonucleotides are attached at functionalized zones of the material surface comprising linear primary amines. The oligonucleotides can be generally attached to the particles as follows. The amines carry a positive charge at neutral pH, allowing attachment of native DNA through the formation of ionic bonds with the negatively charged phosphate backbone. Electrostatic attachment can be supplemented by treatment of the polymer surface with ultraviolet light, which induces free radical-based coupling between oligonucleotides and carbon on the alkyl amine. The combination of electrostatic bonding and non-specific covalent attachment links native DNA to the substrate surface in a stable manner. This method may be used for the attachment of whole unmodified DNA, ideally those greater than 30-mers, or a slight variant whereby base-by-base synthesis from an amine functionalized surface can be conducted in-situ, as described by Elder et al., "Antisense Oligonucleotide Scanning Arrays", published in DNA Microarrays: A Practical Approach, Editor: M. Schena, (Oxford University Press, 1999, pp. 77-99). Thus, the desired oligonucleotide sequences can be built up as required to form n-mers on demand in a number of process steps equal to n, without incurring additional retooling costs. Sequences are, therefore, fully user-determined and fully traceable.

V. Coding the Particles.

The coding mechanism used in the present invention relies on attachment of sample molecules to select areas or portions of the surface of the particles. Since the sample molecules readily attach to the surface of the particle having a functionalized binding moiety (i.e., having —$NH_2$ groups thereon) the invention provides for spatially distributed codes by selectively modifying the surface of the particles to allow for binding only in certain portions or zones of the material. This selective modification can be accomplished by selectively modifying or functionalizing the surface only in certain defined portions or zones, or alternatively by fully modifying or functionalizing the surface of the material and then removing the functional binding moieties in certain defined portions or zones. Thus, when a binding event occurs between target and probe in the functionalized zones with concomitant emission of electromagnetic radiation, a detectable distinction between the functionalized and differentially-functionalized zones occurs, revealing the spatially distributed code of the particle, and identifying the binding of target and probe. As used herein, the term "differentially-functionalized zones" refers to zones of the particle surface that have a different functionalization than the "functionalized" zones. For example, the differentially functionalized zone can have different functional binding moieties than the functionalized zones such that the differentially functionalized zones do not preferentially bind probes and/or targets and/or electromagnetic radiation emitting species. Alternatively, the differentially-functionalized zones can comprise no functionalization.

In the practice of the invention, the code can be formed by an ordered or random arrangement of the functionalized and differentially functionalized zones on the surface of the material. For example, the zones can be arranged as bars, bands, holes, bulls eyes, zebra stripes, spots, finger prints, and variations and combinations thereof.

In a preferred embodiment, coding is in the form of a series of functionalized bands interspersed with differentially-functionalized bands on the particle. This can be accomplished, for example, by exposing particular areas of the surface of the material with a laser, e.g., a UV-excimer laser, prior to the filament being cut into particles. The same result could be achieved by exploiting the fact that polymer extrusion processes can incorporate coatings that block ultraviolet light. A photo-modifiable polymer could be substituted for such a coating. The idea here would be to use the polymer as a mask, removing sections with a suitable wavelength light source prior to plasma treatment. In both embodiments, the laser/light source can be programmed to expose the areas of the material which allow a series of functionalized bands of material and differentially-functionalized surface zones (together depicting the codes) for each particle. This is continually accomplished at the filament stage where the filament is advanced past the laser source and rotated so as to ensure correct width and depth of bands. Thereafter, a portion of the filament equal to the length of a particle is cut by the laser yielding an optically readable, coded, cylindrical particle having a predetermined length.

In a preferred embodiment, the particle is formed in the shape of a rod of material and the coding of the particle is in the form of a series of bands of functionalized binding moieties alternating with bands containing differentially-functionalized binding moieties. The codes are read by utilizing the electromagnetic radiation produced by the electromagnetic radiation emitting species attached at the functionalized or modified areas. For example, when the electromagnetic radiation is a fluorescent emission produced by a successful binding of sample oligonucleotide to complementary oligonucleotide probes, fluorescent emission in the functionalized areas acts to illuminate these areas so they can be read by, for example, fluorescence slit profiling. In essence, because the binding event only occurs in the areas that are functionalized bands and not between them, the electromagnetic radiation emission may envisioned as a binary code similar to barcoding with the functionalized zone or band representing 1 and an differentially-functionalized zone or band representing 0. In this embodiment, if a particle has a length of, e.g., 130 µm and each band is, e.g., 5 µm in width, then a total of 26 bands could be produced, i.e. 26 bits. This would yield $2^{26}$ or 67,108,864 possible different codes. In such an embodiment, not all the bits are typically used for codes but are reserved for error checking. Thus the number of possible codes required would depend on the error checking scheme chosen. Using Bi-Phase or Manchester Coding, for example, and ensuring an even power distribution across the coded area, only 50% of the bits would be used for coding. Thus, $2^{13}$ or 8192 different codes would be available for the particles. Such a code-space is particularly applicable to a wide range of sequencing applications including SNP applications which typically require somewhere between 100 and 5000 different codes.

The width of the bands are generally between about 1 µm and 50 µm, and most preferably between approximately 1 µm and 5 µm.

VI. Particle Based Assay Methodology.

The particles of the invention can be applied to various liquid-based assays to perform quantitative, semi-quantitative, qualitative, or ratiometric determinations of targets in solution. Such assays include, but are not limited to SNP detection, hybridization assays, enzymatic extensions and immunoassay techniques such as sandwich assays, competitive assays, and displacement assays. Thus, for example, the invention provides a method for quantitatively assaying the binding of the probe with its identification code and its corresponding target. In such a configuration, oligomers or binder proteins (for example, MABs) that serve as 'probes' would be attached to functionalized areas of the particle surface. On exposure of the particle to sample containing target nucleotides or proteins (e.g., at time=0), mixing would ensure mass-transfer independent binding of target to probe coated particle. Assuming the nucleotides or binder protein to have a high affinity for the target, and low cross-reactivity with others, the amount of target material bound at defined points in time would be a function of the concentration of targets in the sample. For nucleotides, an attached reporter fluorophore would provide information of its presence. For proteins subsequent exposure to a suitable secondary antibody to which a reporter fluorophore is attached would provide information of its presence. The reporter would also reveal its concentration relative to an established standard (quantitative or semi-quantitative), or, relative to other target proteins present in the same sample but bound to different particles (ratiometric).

In one embodiment, the invention provides a method of determining the sequence of an unknown oligonucleotide species in a solution comprising providing a labeled oligonucleotide library of particles according to the invention, wherein the oligonucleotide sequence of each oligonucleotide attached to each particle in the library and the characteristic electromagnetic emission intensity profile of each particle in the library is stored and correlated in a database, mixing the solution with the labeled oligonucleotide library under conditions sufficient to permit the unknown oligonucleotide speices to hybridize with corresponding particles of the labeled oligonucleotide library, exciting the particles to produce the characteristic electromagnetic emission intensity profile corresponding to the particle(s) in the library, detecting the characteristic electromagnetic emission intensity profile and correlating it to the characteristic emission intensity profile in the database, thereby determining the sequence of the unknown oligonucleotide species.

In the practice of this method the characteristic emission profile can be detected by a charged coupling device (CCD) array, photodiode array, or photomultiplier tube. Typically a laser is used to excite the particles, however other similar electromagnetic emission excitation device are equally applicable.

In the practice of the invention the unknown oligonucleotide species can be, e.g., a single nucleotide polymorphism (SNP), cDNA cloned from RNA expressed by a normal cell or cDNA cloned from RNA expressed by a cell that has been subjected to a drug, toxic agent, or other chemical substance.

In other embodiments, the invention also provides a method for detecting a genetic mutation in a PCR product amplified from a nucleic acid sample containing a target gene of interest, comprising the steps:

(a) selecting an oligonucleotide probe, said oligonucleotide probe including a polymorphic site, said polymorphic site including said genetic mutation or the wild type sequence found at the analogous position of said genetic mutation in a wild type target gene;

(b) coupling said oligonucleotide probe to one of a plurality of particles of a library of particles according to to the invention to form a labeled probe library;

(c) providing PCR products comprising the region of said target gene amplified by PCR;

(d) mixing the labeled probe library and the PCR products;

(e) incubating said mixture under hybridization conditions, wherein if said PCR products include said polymorphic site, said PCR products bind to a particle(s) of said oligonucleotide probe library;

(f) exciting the particles to produce the characteristic electromagnetic emission intensity profile corresponding to the particle(s) in the library, (g) detecting the characteristic electromagnetic emission intensity profile of the particle(s); and (h) detecting said genetic mutation, or absence thereof, as a function of the measured characteristic electromagnetic emission intensity profile of the particle(s).

In another embodiment, the invention provides a method for determining the amount of a target compound in a test sample comprising the steps of incubating a mixture of a test sample suspected of containing the target compound with at least one particle according to to the invention, wherein the particle(s) comprise a plurality of an antibody which is specific for the target compound, under conditions appropriate to form target/antibody complexes, wherein the electromagnetic radiation emission occurs upon formation of the target/antibody complex, and measuring the amount of electromagnetic radiation present in said mixture thereby determining the amount of target compound in said test sample.

The invention also provides an assay for the detection of binding between a probe and a target comprising contacting the probe with a solution suspected of containing the target, wherein the probe is attached to a particle which emits electromagnetic radiation upon binding between probe and target and emits electromagnetic radiation as a means of identifying the particle in solution.

In one embodiment of the assay, the particle comprises a single electromagnetic radiation emitting species that emits both the electromagnetic radiation upon binding between probe and target and the electromagnetic radiation as a means of identifying the particle in solution. In another embodiment of the assay, the particle comprises different electromagnetic radiation emitting species to emit the electromagnetic radiation upon binding between probe and target and to emit the electromagnetic radiation as a means of identifying the particle in solution. In the practice of the assay, the electromagnetic radiation emitted as a means of identifying the particle is emitted as a pattern of electromagnetic radiation, wherein the pattern is formed by attaching the electromagnetic radiation emitting species to functionalized zones on the surface of the particle spatially distributed among differentially functionalized zones on the surface of the particle that do not contain the electromagnetic radiation emitting species.

Figure 2:
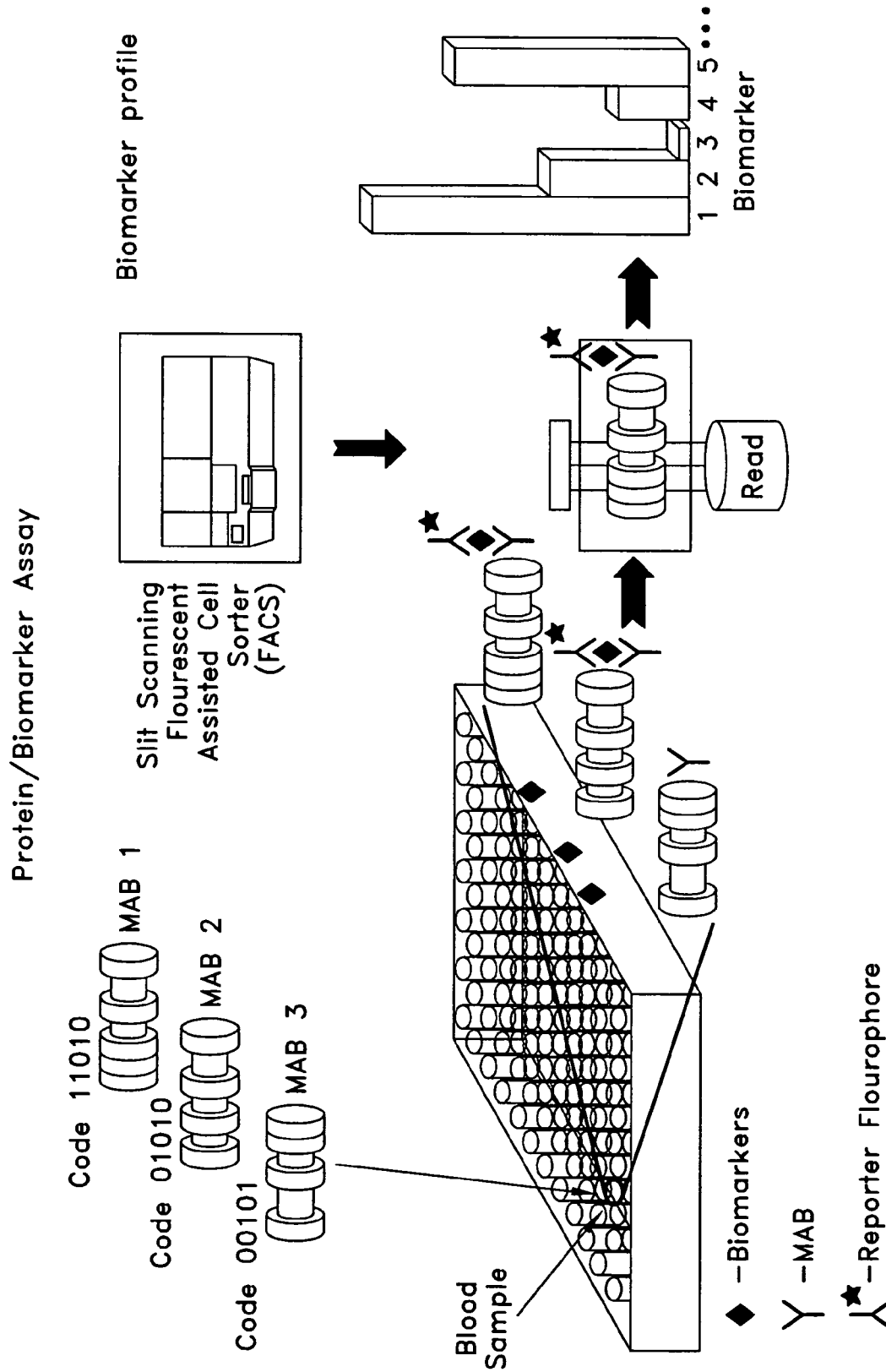
FIG. 2 illustrates a preferred embodiment of a particle based assay method of the invention for a biomarker assay.
Figure 3:
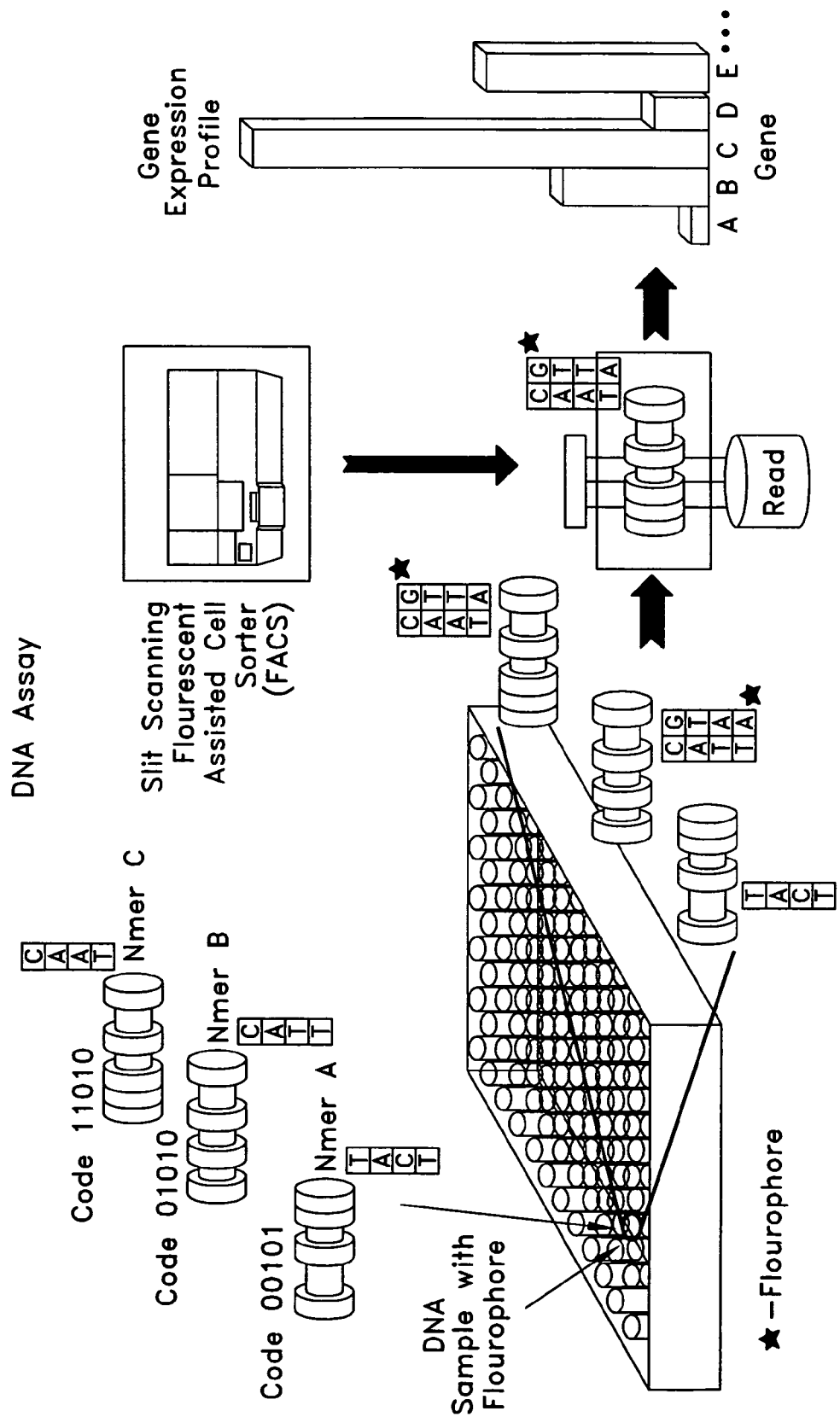
FIG. 3 illustrates a preferred embodiment of a particle based assay method of the invention for a DNA assay.

Preferred embodiments of particle based assay methods are depicted in FIG. 2, in which a fluorescent-labeled sample protein as shown is mixed with the coded particles and FIG. 3 in which a fluorescent-labeled sample DNA is mixed with the coded particles. After a predetermined period of time, the particles are flowed past a laser source of the flow cytometer as shown in a sandwich assay on FIG. 2 (or DNA with fluorophore in FIG. 3) The laser excites the fluorophore which has attached itself to probe/target, either monoclonal antibody in FIG. 2 or cDNA/N-mer in FIG. 3 on the particle, whereby any binding is indicated by a high intensity fluorescent emission detected by a CCD camera. The code may then be read by fluorescent slit profiling, in which the fluorescent bands are viewed as a series of peaks (corresponding to the bands having an attached fluorophore) and troughs (areas between bands) whose width and separation is characteristic of the particle's code. The CCD outputs the resultant fluorescent energy waveform to the computer containing the sample-particle database (library). The computer than compares the distances between the peaks of the waveform, to the distances between bands of cataloged particles to find the particular cataloged particle. Once the particle is found in the database, the unknown protein or DNA sample is then determined.

EXPERIMENTAL DETAILS

Example 1

Particle Material Surface Functionalization

A polypropylene filament was subjected to the radio frequency (RF) discharge method which involves exposing the polymer to an ammonia plasma, using substantially the method as disclosed by Beckman Instruments (See, Matson, R. S., Rampal J. B. and Coassin P. J., Biopolymer Synthesis on Polypropylene Supports, Anal. Biochem., (1994) 217, 306-310). The process is automated, robust, the whole surface is exposed, and many filaments can be treated at the same time. The plasma process parameters were as follows:
    gas: ammonia,
    chamber pressure: 25-30 Pa
    gas flow rate: 35 cubic centimeters per second
    treatment time: 90 seconds.

X-ray photoelectron spectroscopy (XPS) and scanning electron microscopy (SEM) surface characterization techniques were used to analyze the results of the treatment process. The aim of the XPS was to characterize the surfaces of two filament samples, by determination of the surface concentration and chemical state of detectable elements. Both samples contained carbon (as C—(C,H), C—(O,N), and C=O), oxygen, nitrogen (as C—N and $R_4$—$N^+$), and phosphorus (as $PO_x$). The aminated filament also contained carbon (as (O,N)—C=O), chlorine (as $Cl^-$), and silicon (as silicon and/or silicate), while having an increased concentration of oxygen and a three-fold increase in nitrogen relative to the control sample. Quantification of the elements was accomplished by using the atomic sensitivity factors for a Physical Electronics Model 5700LSci ESCA Spectrometer analytical conditions: X-ray source (monochromatic Al); source power (350 W); analysis region (2 mm×0.8 mm); exit angle (50°). The plasma process creates precursor —$NH_2$ and —NH groups which diffuse through the chamber to the polymer substrate. Successful surface amination was confirmed by the attachment of primary amine specific FITC (FIGS. 4(A) and 4(B)). Both plasma treated and non plasma treated surfaces were exposed to FITC. FITC was not observed to bind on the non plasma treated surface. Images were taken with a fluorescence microscope. FIG. 4(A) shows the polypropylene surface prior to plasma treatment; FIG. 4(B) shows the polypropylene surface following plasma treatment (each is further depicted in a drawing below the corresponding photomicrograph). The images were captured by an Olympus IMT-2 inverted microscope coupled so a 75-W Xenon arc lamp and fitted with an interference filter and an IR filter. The image was formed on a Princeton Instruments thermoelectrically-cooled CCD camera (Model TE/CCD-500B with an ST-130 controller). The 518×384 pixel images had a resolution of 1.2 μm and a dynamic resolution of 16-bits. Colors were achieved by a combination of suitable filtering and mathematical modeling. Excitation wavelengths in the 480-500 nm range were used.

FIG. 4(A) demonstrates both the low-background of polypropylene (i.e., low auto-fluorescence) as well as the fact that amine-specific FITC does not bind to it. Low auto-fluorescence is important in order to reduce background noise during fluorescence profiling (when the code is being 'read'). Polymers (such as polyamide) tend to have a high auto-fluorescence, so its low level is a significant advantage here.

Example 2

Laser Ablation of Particles

Polypropylene filament was etched by a 248 nm UV-excimer laser to ablate areas of functionalized polymer in order to expose underlying inert and, therefore, differentially-functionalized, material. A Potomac LMT-4000 was used to create grooves of 10 μm wide The system contained a Potomac TGX-1000 KrF (248 nm) excimer laser configured for focused operation at the polymer surface. The laser beam was apertured in order to achieve a 5 μm spot size at the surface. The maximum pulse repetition rate was 2 KHz with a maximum pulse energy of 45 μJ. The photon energy of about 4 to 7 eV at UV wavelengths is about 30 to 40 times greater than that of $CO_2$ laser radiation. Consequently, there is a vast difference in laser-material interactions. Most organic polymers absorb strongly in the UV, and laser ablation in this spectral range produces sharp edges and a lack of charring when contrasted with that performed by long-wavelength devices such as $CO_2$ lasers. Since the absorption coefficient for UV light is very high for most materials, the energy is absorbed in a very thin surface layer. Subsequent attachment of fluorescent substances as described in Example 1 to the non-ablated active areas will reveal the code.

Having presented the invention in view of the above described embodiments, various alterations, modifications, and improvements are intended to be within the scope and spirit of the invention. The foregoing description is by way of example only and is not intended as limiting. The invention's limit is defined only in the following claims and the equivalents thereto.

What is claimed is:

1. A uniquely coded target-specific particle for detecting the presence of molecules of a specific target in a solution, the target-specific particle comprising:
    a plurality of functionalized zones comprising functional binding moieties configured to bind with the target molecules and a plurality of differentially-functionalized zones configured to not bind with the target molecules;
    wherein the plurality of functionalized zones and the plurality of differentially-functionalized zones are arranged on the target-specific particle in a spatially-distributed pattern which is unique to that target-specific particle, whereby to create a unique particle code for that target-specific particle, with the unique particle code being correlated with the binding capabilities and the spatially-distributed binding sites of the target-specific particle;
    whereby, (i) when the target-specific particle is introduced into a solution containing optically-labeled target molecules which are capable of emitting electromagnetic radiation, the optically-labeled target molecules bind to the plurality of functionalized zones of the target-specific particle so that the target molecules are bound to the target-specific particle in the spatially-distributed pattern which is unique to that target-specific particle, and (ii) when the target-specific particle with the target molecules bound thereto is thereafter passed through an appropriate reader, the electromagnetic radiation emitted by the optically-labeled target molecules bound to the plurality of functionalized zones of the target-specific particle appear in the spatially-distributed pattern which is unique to that target-specific particle, thereby identifying the target-specific particle with its bound target molecules, and detecting the presence of the target molecules in the solution.

2. The target-specific particle of claim 1, wherein the optically-labeled target emits electromagnetic radiation within the range from ultraviolet to infrared.

3. The target-specific particle of claim 1, wherein the optically-labeled target emits electromagnetic radiation between 400 nm to 1 µm.

4. The target-specific particle of claim 1, wherein the optically-labeled target emits electromagnetic radiation of differing intensities.

5. The target-specific particle of claim 1, wherein (i) the target-specific particle has a given length, and (ii) each of the portions has a length which is at least an order of magnitude less than the length of the target-specific particle.

6. The target-specific particle of claim 5, wherein the length of each of the portions is between 1 µm and 50 µm.

7. The particle of claim 1, wherein the particle has a shape chosen from the group consisting of cylindrical, spherical, conical, elliptical, bar-like, slab-like, ribbon-like, ovoid, spiral, amoeba-like, tube-like, and combinations thereof.

8. The particle of claim 7 wherein the particle has a width to length ratio which is from about 1:2 to about 1:10.

9. The particle of claim 7, wherein the particle has a width to length ratio which is from about 1:3 to about 1:5.

10. The particle of claim 1, wherein the surface of the particle is chosen from the group consisting of flat, curved, rough, smooth, undulating and combinations thereof.

11. The particle of claim 1, wherein the particle is formed from a material chosen from the group consisting of polymers, composites, inorganics, natural products, and combinations thereof.

12. The particle of claim 11, wherein the polymers are chosen from the group consisting of polypropylene, polyethylene, polyacetylene, polypyrrole, conducting polymers, and combinations thereof.

13. The particle of claim 11, wherein the composites are chosen from the group consisting of glass fiber composites, carbon fiber composites, and combinations thereof.

14. The particle of claim 11, wherein the natural products are chosen from the group consisting of silk, wax, rubber, resins, and combinations thereof.

15. A system for detecting the presence of molecules of a plurality of specific targets in a solution, the system comprising:
    a plurality of different target-specific particles, wherein each of the different target-specific particles comprises:
        a plurality of functionalized zones comprising functional binding moieties configured to bind with the target molecules and a plurality of differentially-functionalized zones configured to not bind with the target molecules;
        wherein the plurality of functionalized zones and the plurality of differentially-functionalized zones are arranged on the target-specific particle in a spatially-distributed pattern which is unique to that target-specific particle, whereby to create a unique particle code for that target-specific particle, with the unique particle code being correlated with the binding capabilities and the spatially-distributed binding sites of the target-specific particle; and
    a solution containing a plurality of optically-labeled targets, the optically-labeled targets being capable of emitting electromagnetic radiation;
    whereby, (i) when the plurality of different uniquely coded target-specific particles for detecting the presents of molecules of a plurality of targets in the solution, wherein each of the target-specific particles binds the molecules of a specific target is introduced into the solution containing the optically-labeled target molecules, the optically-labeled target molecules bind to the plurality of functionalized zones of the appropriate target-specific particles so that the target molecules are bound to the appropriate target-specific particles in the spatially-distributed pattern which is unique to those target-specific particles, and (ii) when the target-specific particles with the target molecules bound thereto are thereafter passed through an appropriate reader, the electromagnetic radiation emitted by the optically-labeled target molecules bound to the plurality of functionalized zones of the target-specific particles appears in the spatially-distributed pattern which is unique to those target-specific particles, thereby identifying those target-specific particles with bound target molecules, and detecting the presence of the target molecules in a solution.

16. The system of claim 15, wherein the optically-labeled target emits electromagnetic radiation within the range from ultraviolet to infrared.

17. The system 15, wherein the optically-labeled target emits electromagnetic radiation between 400 nm to 1 µm.

18. The system of claim 15, wherein the optically-labeled target emits electromagnetic radiation of differing intensities.

19. The system of claim 15, wherein (i) the target-specific particle has a given length, and (ii) each of the portions has a length which is at least an order of magnitude less than the length of the target-specific particle.

20. The system target-specific particle of claim 19, wherein the length of each of the portions is between 1 µm and 50 µm.

21. The particle of claim 15, wherein the particle has a shape chosen from the group consisting of cylindrical, spherical, conical, elliptical, bar-like, slab-like, ribbon-like, ovoid, spiral, amoeba-like, tube-like, and combinations thereof.

22. The particle of claim 21 wherein the particle has a width to length ratio which is from about 1:2 to about 1:10.

23. The particle of claim 21, wherein the particle has a width to length ratio which is from about 1:3 to about 1:5.

24. The particle of claim 15, wherein the surface of the particle is chosen from the group consisting of flat, curved, rough, smooth, undulating and combinations thereof.

25. The particle of claim 15, wherein the particle is formed from a material chosen from the group consisting of polymers, composites, inorganics, natural products, and combinations thereof.

26. The particle of claim 25, wherein the polymers are chosen from the group consisting of polypropylene, polyethylene, polyacetylene, polypyrrole, conducting polymers, and combinations thereof.

27. The particle of claim 25, wherein the composites are chosen from the group consisting of glass fiber composites, carbon fiber composites, and combinations thereof.

28. The particle of claim 25, wherein the natural products are chosen from the group consisting of silk, wax, rubber, resins, and combinations thereof.

* * * * *